(12) United States Patent
Stewart

(10) Patent No.: US 9,700,238 B2
(45) Date of Patent: Jul. 11, 2017

(54) JOINT MOTION SENSING TO MAKE A DETERMINATION OF A POSITIONAL CHANGE OF AN INDIVIDUAL

(75) Inventor: Robert E. Stewart, Woodland Hills, CA (US)

(73) Assignee: Northrop Grumman Systems Corporation, Fall Church, VA (US)

( * ) Notice: Subject to any disclaimer, the term of this patent is extended or adjusted under 35 U.S.C. 154(b) by 260 days.

(21) Appl. No.: 13/134,208

(22) Filed: Jun. 1, 2011

(65) Prior Publication Data

US 2011/0238366 A1    Sep. 29, 2011

Related U.S. Application Data

(62) Division of application No. 10/681,529, filed on Oct. 8, 2003, now Pat. No. 7,981,057.

(60) Provisional application No. 60/418,119, filed on Oct. 11, 2002.

(51) Int. Cl.
| | |
|---|---|
| *A61B 5/11* | (2006.01) |
| *G06F 15/00* | (2006.01) |
| *G01C 21/00* | (2006.01) |
| *A41D 13/02* | (2006.01) |
| *G01C 21/16* | (2006.01) |
| *G01C 22/00* | (2006.01) |
| *A61B 5/00* | (2006.01) |
| *G01S 19/19* | (2010.01) |

(52) U.S. Cl.
CPC ............ *A61B 5/1113* (2013.01); *A41D 13/02* (2013.01); *A61B 5/1112* (2013.01); *A61B 5/1126* (2013.01); *G01C 21/16* (2013.01); *G01C 22/006* (2013.01); *A61B 5/4528* (2013.01); *A61B 5/6804* (2013.01); *A61B 5/6807* (2013.01); *G01S 19/19* (2013.01)

(58) Field of Classification Search
CPC ....... G01C 22/006; G01C 21/005; A61B 5/11; A61B 5/1112; A61B 5/1116; A61B 5/112
USPC .................................. 600/587, 595; 702/150
See application file for complete search history.

(56) References Cited

U.S. PATENT DOCUMENTS

| | | | | |
|---|---|---|---|---|
| 5,583,776 A | * | 12/1996 | Levi et al. ..................... | 701/400 |
| 6,132,391 A | * | 10/2000 | Onari et al. ................... | 600/595 |
| 2003/0083596 A1 | * | 5/2003 | Kramer et al. ............... | 600/595 |

OTHER PUBLICATIONS

Judd, C. Tom. A Personal Dead Reckoning Module. Presented at Institute of Navigation's ION GPS '97. Kansas City, MO. Sep. 1997.*
Dingwell, JB et al. "Increased variability of continuous overground walking in neuropathic patients is only indirectly related to sensor loss" Gait and Posture. 2001; pp. 1-10.*
Trnkoczy, Amadej, and Tadej Bajd. "A simple electrogoniometric system and its testing." Biomedical Engineering, IEEE Transactions on 3 (1975): 257-259.*

* cited by examiner

*Primary Examiner* — Michael C Stout
*Assistant Examiner* — Nicholas E Kolderman
(74) *Attorney, Agent, or Firm* — Patti & Malvone Law Group, LLC

(57) ABSTRACT

An apparatus in one example comprises one or more sensors that produce one or more signals based on one or more joint motions of an individual, and one or more processing components that employ one or more of the one or more signals to make a determination of a positional change of the individual.

10 Claims, 4 Drawing Sheets

JOINT MOTION SENSING TO MAKE A DETERMINATION OF A POSITIONAL CHANGE OF AN INDIVIDUAL

CROSS-REFERENCE TO RELATED APPLICATION

This application claims the priority of U.S. utility patent application Ser. No. 10/681,529, filed by Robert E. Stewart on Oct. 8, 2003 and entitled "JOINT MOTION SENSING TO MAKE A DETERMINATION OF A POSITIONAL CHANGE OF AN INDIVIDUAL" and claims the priority of U.S. provisional patent application 60/418,119, filed by Robert E. Stewart on Oct. 11, 2002, and entitled "STRAIN SENSOR EMPLOYMENT OF JOINT MOTION TO DETERMINE LOCATION OF BODY" of which the entire contents of both applications are incorporated herein by reference.

TECHNICAL FIELD

The invention in one example relates generally to sensing and more particularly to motion detection.

BACKGROUND

An inertial navigation system ("INS") and a global positioning system ("GPS") generate position information on an individual. The inertial navigation system and the global positioning system generate complementary position information. The position information generated by the global positioning system may be used to correct the position information generated by the inertial navigation system for some measurements. The position information generated by the inertial navigation system may be used during reacquisition of satellites by the global positioning system. A filter (e.g., a Kalman filter) is used to weigh and combine the position information received from the inertial navigation system and the global positioning system. The accuracy of the position information on the individual is dependent on the reliability and availability of the inertial navigation system and the global positioning system. If either the inertial navigation system or the global positioning system become unreliable and/or unavailable, then the position information determined by the filter becomes less accurate. If both the inertial navigation system and the global positioning system become unreliable and/or unavailable, then no position information is generated.

As one shortcoming, the inertial navigation system has a position error (e.g., drift) that builds up over time. As the elapsed time of operation increases, the position information generated by the inertial navigation system becomes less accurate. There are times when the elapsed time of operation is long compared to the drift performance of the inertial navigation system. During such times, the position information determined by the filter becomes less accurate.

As another shortcoming, there are times when the global positioning system is unavailable due to jamming or interference. During such times, the position information determined by the filter becomes less accurate.

As yet another shortcoming, upon initialization and/or re-initialization, the inertial navigation system requires a starting and/or restarting position to begin generating the position information of the individual. Without the external input of the starting and/or restarting position, the inertial navigation system is unable to begin navigation. Also, upon initialization and/or re-initialization, a delay exists between the start of initialization and/or re-initialization and when the global positioning system is able to begin navigation. The delay is reduced if upon initialization and/or re-initialization the starting and/or restarting position of the global positioning system is available. There are times when an accurate starting and/or restarting position is unavailable.

SUMMARY

The invention in one implementation encompasses an apparatus. The apparatus comprises one or more sensors that produce one or more signals based on one or more joint motions of an individual, and one or more processing components that employ one or more of the one or more signals to make a determination of a positional change of the individual.

Another implementation of the invention encompasses a method. One or more movements of one or more joints of an individual are measured. The one or more movements are translated into a positional change of the individual.

Yet another implementation of the invention encompasses an article. The article comprises a computer-readable signal-bearing medium. The article includes means in the medium for measuring one or more movements of one or more joints of an individual. The article includes means in the medium for translating the one or more movements into a positional change of the individual.

DESCRIPTION OF THE DRAWINGS

Features of exemplary implementations of the invention will become apparent from the description and the accompanying drawings in which.

DETAILED DESCRIPTION

Figure 1:
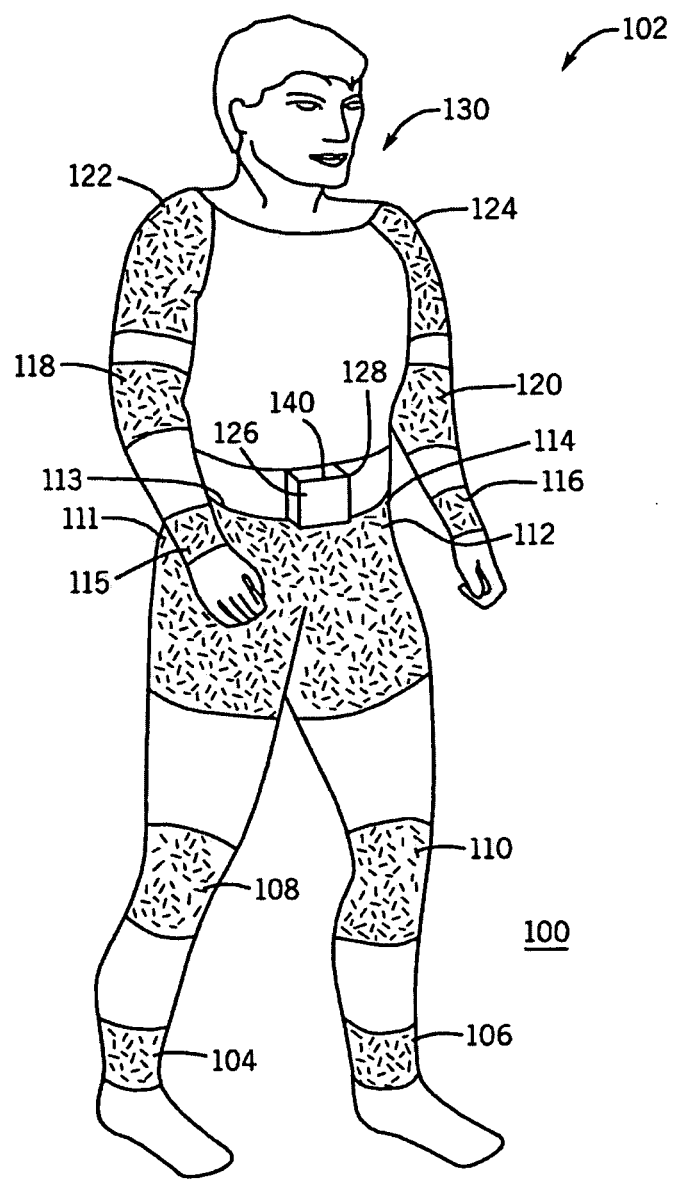
FIG. 1 is a representation of one exemplary implementation of an apparatus that comprises one or more sensors, a processing component, and a navigation component.

Turning to FIG. 1, an apparatus 100 in one example comprises one or more sensors and a processing component for measuring a movement of a body, for example an individual. The one or more sensors are strategically located on one or more joints of the individual. The one or more sensors measure movements of the one or more joints in one or more directions. The processing component translates (e.g., calculates, converts, infers, deduces, determines, and/or extrapolates) the movements of the one or more joints into a general movement of the individual. The general movement represents an overall movement of the individual. The apparatus 100 includes a plurality of hardware and/or software components. A number of such components can be combined or divided in the apparatus 100.

In one example, the apparatus 100 employs at least one computer-readable signal-bearing medium. One example of a computer-readable signal-bearing medium for the apparatus 100 comprises an instance of a recordable data storage medium 201 (FIG. 2) such as one or more of a magnetic, electrical, optical, biological, and atomic data storage medium. In another example, a computer-readable signal-bearing medium for the apparatus 100 comprises a modulated carrier signal transmitted over a network comprising or coupled with the apparatus 100, for instance, one or more of a telephone network, a local area network ("LAN"), the internet, and a wireless network. An exemplary component of the apparatus 100 employs and/or comprises a set and/or series of computer instructions written in or implemented with any of a number of programming languages, as will be appreciated by those skilled in the art.

In one example, the apparatus 100 comprises an anthropometric dead reckoning motion detector for a body. "Anthropometric" as used herein in one example refers to measurement of the body. "Dead reckoning" as used herein in one example refers to navigating by measuring the course and distance traveled from a known point. In one example, the body comprises an individual 102. For example, the individual 102 comprises a person, animal, or robot. The anthropometric dead reckoning motion detector takes measurements of the individual 102 and converts the measurements to a position change starting from a known location.

The apparatus 100 comprises one or more sensors, for example one or more of bi-lateral ankle sensors 104 and 106, knee sensors 108 and 110, hip sensors 111 and 112, waist sensors 113 and 114, wrist sensors 115 and 116, elbow sensors 118 and 120, shoulder sensors 122 and 124, a processing component 126, and a navigation component 128. In one example, one or more of the sensors comprise strain sensors, as described herein. In another example, one or more of the sensors comprise rate sensors, for example, low cost rate sensors. The one or more sensors serve to measure a movement of one or more joints of the individual 102. For example, the one or more sensors measure three dimensional motion of the one or more joints, such as the ankle, knee, hip, waist, wrist, elbow, and/or shoulder of the individual 102.

As the individual 102 traverses a path from a known starting location, the apparatus 100 serves to measure the movement of the one or more joints of the individual 102 and record the movement. Subsequently, the movement of the one or more joints of the individual 102 is reconstructed to determine the path of the individual 102.

The one or more sensors are arranged bi-laterally on the individual 102. The one or more sensors may be arranged symmetrically or asymmetrically on the individual 102. The one or more sensors may measure other joint locations, in addition to the ankle, knee, hip, waist, wrist, elbow, and/or shoulder of the individual 102. The one or more sensors monitoring the one more joints on the lower body of the individual 102 provide information to reconstruct a locomotion of the individual 102. For example, the information generated by the ankle sensors 104 and 106, knee sensors 108 and 110, hip sensors 111 and 112, and waist sensors 113 and 114 translate to the locomotion of the individual 102. The information generated by the one or more sensors may also be translated to measure critical points along the path such as abrupt turns or elevation changes.

The one or more sensors measure a direction and a displacement of the movement. In one example, a first sensor measures the direction of the movement and a second sensor measures the displacement of the movement. In another example, the first and second 25 sensors measure both the displacement and direction of the movement.

The one or more sensors comprise strain sensors. The strain sensors detect a bending strain and/or a twisting strain due to the movement of the one or more joints of the individual 102. For example, the ankle sensors 104 and 106 detect the bending strain and/or the twisting strain due to the movement of the ankle joint. The bending strain corresponds to, and may be translated to, the displacement (e.g., meters) of the movement. The twisting strain corresponds to, and may be translated to, the direction (e.g., degrees) of the movement.

In one example, the one or more sensors are embedded in a suit 130 at the one or more joints of the individual 102. The suit 130 is worn by the individual 102. The suit 130 may be worn as outerwear, an undergarment, or incorporated into another suit. The suit 130 may be incorporated into a second suit used to monitor other information such as biological functions of the individual 102 (e.g., heart rate, body temperature, etc.).

Figure 2:
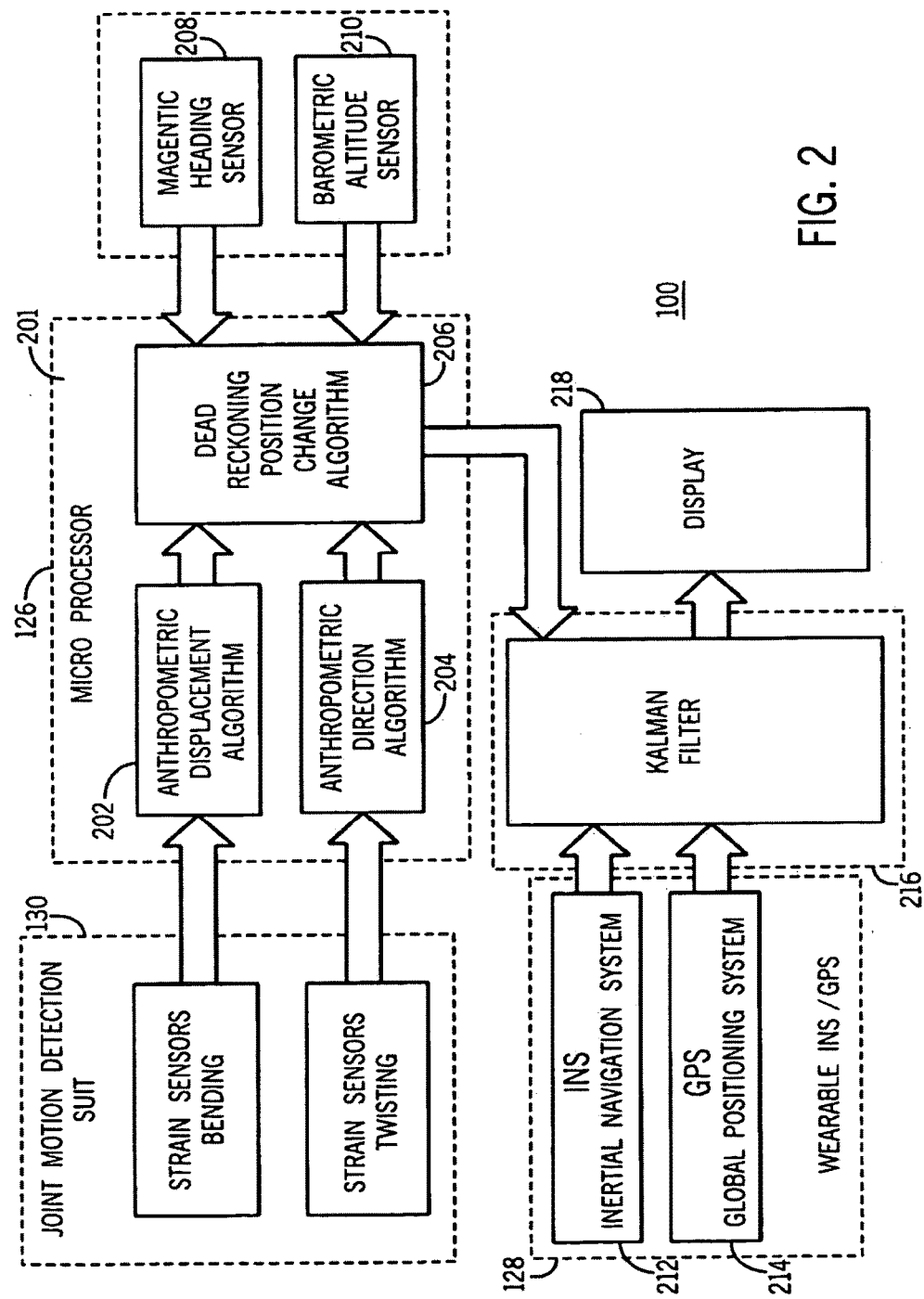
FIG. 2 is a representation of one exemplary flow diagram employable by the apparatus of FIG. 1.

Referring to FIGS. 1-2, the processing component 126 employs one or more algorithms for translating measurements from the one or more sensors into a position change of the individual 102. A first algorithm 202 takes as an input a bending component of the strain experienced by the one or more sensors. The first algorithm 202 translates the bending component into a displacement component of the position change. A second algorithm 204 takes as an input a twisting component of the strain experienced by the one or more sensors. The second algorithm 204 translates the twisting component into a direction component of the position change. A third algorithm 206 takes as inputs the displacement component, the direction component, and a starting location of the position change. The third algorithm 206 translates the displacement component, the direction component, and the starting location of the position change into an updated position of the individual 102. The one or more algorithms and the one or more sensors may be calibrated to the specific motions of the individual 102 by having the individual 102 traverse a known path. The measurements by the one or more sensors generated during traversal of the known path will tune the one or more algorithms to the specific motion of the individual 102. The first, second, and third algorithms may be combined or divided.

The third algorithm 206 may additionally take inputs from a magnetic heading sensor 208 and a barometric altitude sensor 210. The magnetic heading sensor 208 provides additional information on the direction of the movement of the individual 102 to supplement the twisting component of the strain sensors. The magnetic heading sensor 208 would use the Earth's magnetic field to sense the direction of the movement. A change in magnetic field measured by the magnetic heading sensor 208 would correspond to a change of direction by the individual 102. The barometric altitude sensor 210 would measure an atmospheric pressure for altitude position changes. A change in atmospheric pressure measured by the barometric altitude sensor 210 would correspond to a change of altitude by the individual 102. The position information generated by the magnetic heading sensor 208 and the barometric altitude sensor 210 would assist the anthropometric dead reckoning motion detector during motion of the individual 102 while the one or more joints of the individual 102 are not in motion. The third algorithm 206 would weigh and combine the position information generated by the magnetic heading sensor 208 and the barometric altitude sensor 210 with the position information generated by the first and second algorithms 202 and 204.

The navigation component 128 in one example comprises an inertial navigation system 212 ("INS") and/or a global positioning system 214 ("GPS"). The navigation component 128 provides position information of the individual 102 to supplement the position information generated by the processing component 126. In one example, the navigation component 128 is attached to the waist of the individual 102. For example, the navigation component 128 is integrated into a belt for the individual 102.

Figure 4:
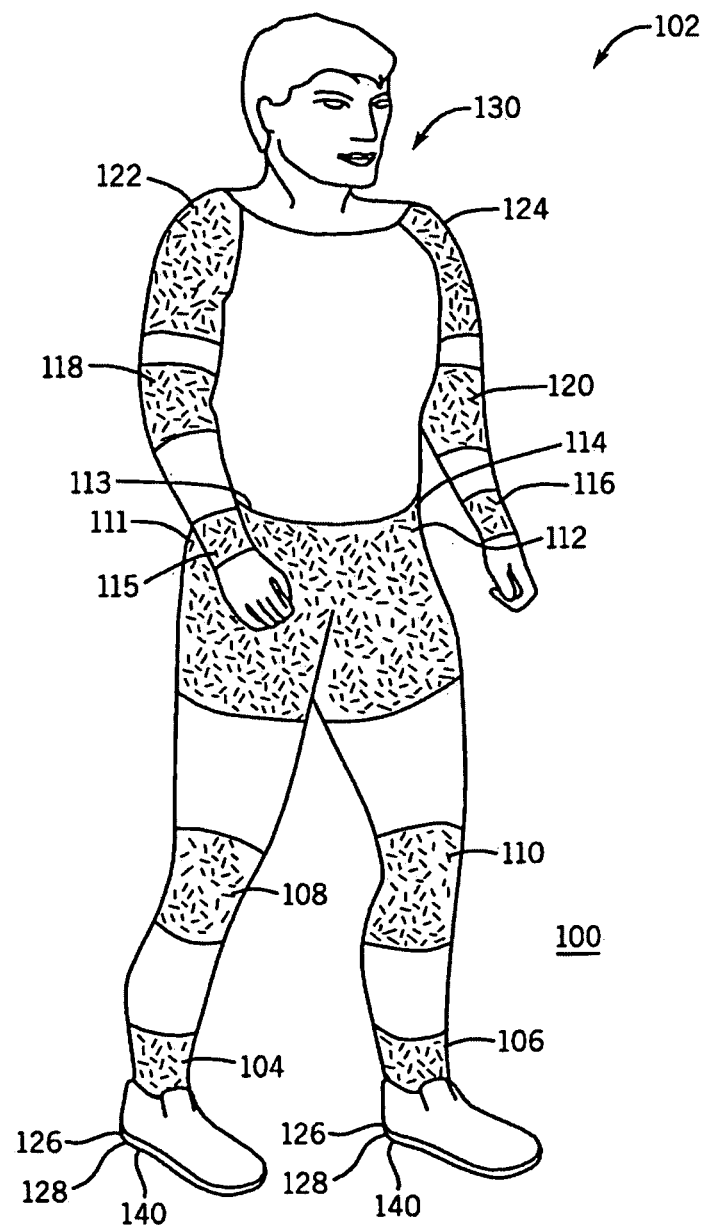
FIG. 4 is another representation of one exemplary implementation of the apparatus that comprises one or more sensors, the processing component, and the navigation component.

Referring to FIG. 4, in another example, the navigation component 128 is located at a heel of the foot of the individual 102. For example, the navigation component 128 is mounted into a shoe or boot worn by the individual 102. Additionally, the processing component 126 and other electronic components may be located with the navigation component 128 in the shoe worn by the individual 102. Locating the navigation component 128 in the shoe allows for zero velocity updates or zero position change updates for the navigation component 128. For example, at a time when the foot of the individual 102 is planted or substantially stationary, the navigation component 128 may initiate the zero velocity update to correct for error or bias in measurements of the navigation component 128.

Referring to FIGS. 1-2, a filtering component 216 comprises an algorithm to weigh and combine the position information generated by the processing component 126, the inertial navigation system 212, and the global positioning system 214. The weighing and combination of the position information is based on the respective reliabilities of the processing component 126, the inertial navigation system 212, and the global positioning system 214. The algorithm processes the measurements of the processing component 126, the inertial navigation system 212, and the global positioning system 214 to deduce an estimate of the position of the individual 102 by using a time sequence of measurements of the system behavior, plus a statistical model that characterizes the system and measurement errors, plus initial condition information. In one example, the filtering component 216 comprises a Kalman filter. In one example, the processing component 126 and the filtering component 216 are combined with the navigation component 128, for example in the inertial navigation system 212. The output of the filtering component 216 may be passed to one or more of a display 218 and a recording device 140.

The recording device 140 stores the position information output from the filtering component 216. A path of the individual 102 may be reconstructed from the known starting location and the recorded position information. The path may be used to create a map of an area previously unmapped, incorrectly mapped, or update outdated maps. Using dead reckoning navigation to provide information for cartography is especially useful in remote areas where the global positioning system 214 is unavailable, or in areas where the global positioning system 214 in experiencing jamming or interference.

Upon initialization and/or re-initialization, the inertial navigation system 212 requires a starting and/or restarting location to begin generating the position information of the individual 102. The dead reckoning position information generated by the processing component 126 may be used as an estimate of the starting and/or restarting location for the inertial navigation system 212. Upon initialization and/or re-initialization, the global positioning system 214 would benefit from the starting and/or restarting position to lock onto satellites. The dead reckoning position information generated by the processing component 126 may be used as an estimate of the starting and/or restarting location for the global positioning system 214.

During the run times, the inertial navigation system 212 and the global positioning system 214 may provide corrections to the one or more sensors and/or the processing component 126. Therefore, the position information generated by the inertial navigation system 212, the global positioning system 214, and the processing component 126 would be in better agreement. Due to the corrections, at a time when the inertial navigation system 212 and/or the global positioning system 214 become unavailable, the processing component 126 would be more able to alone generate an estimate of the position information.

Figure 3:
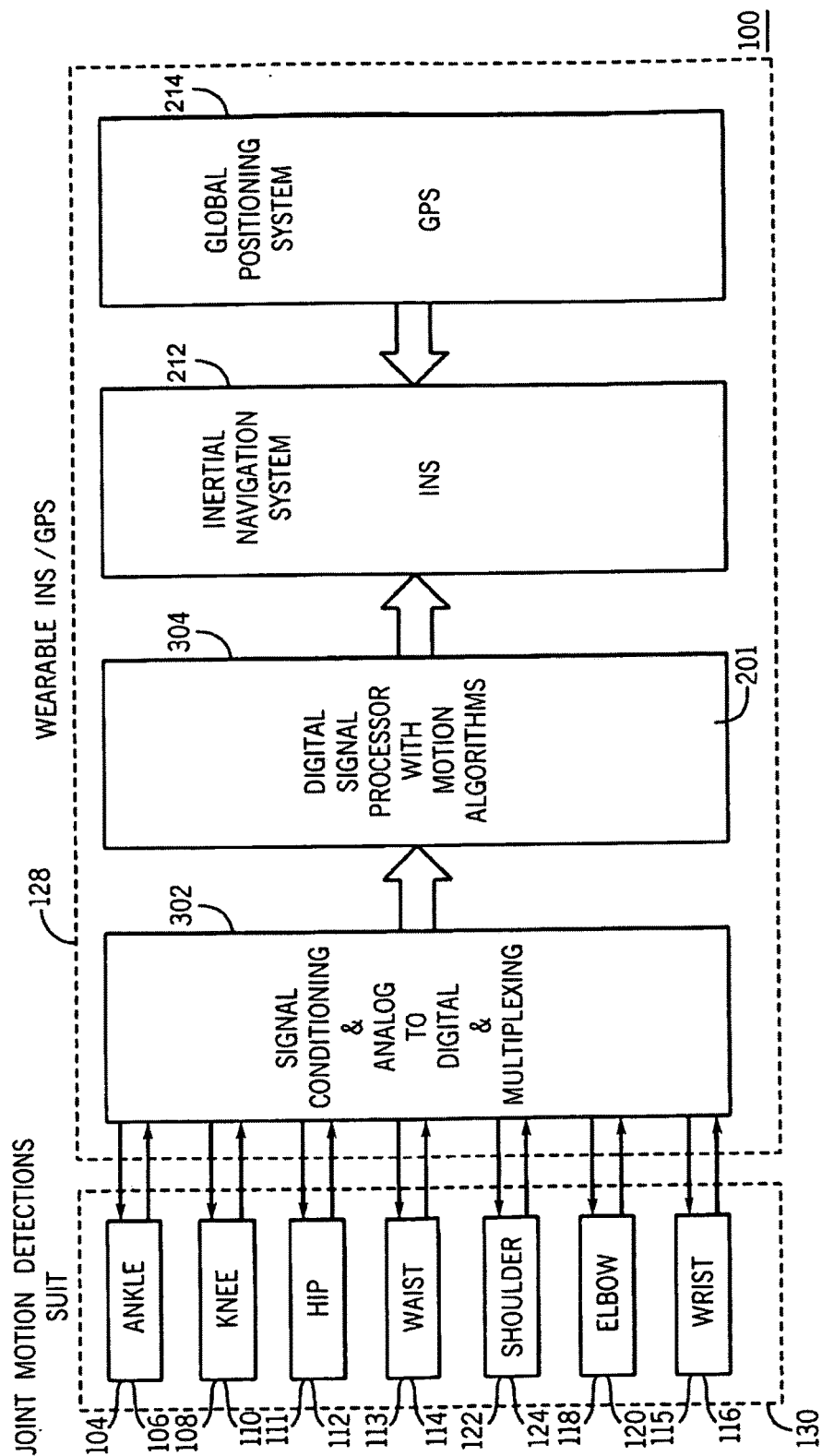
FIG. 3 is a representation of another exemplary flow diagram employable by the apparatus of FIG. 1.

Referring to FIG. 3, in one example the navigation component 128 comprises a signal conditioning component 302, a signal processor 304, and zero or more of the inertial navigation system 212 and the global positioning system 214. The one or more sensors of the suit 130 pass information to the navigation component 128. The signal conditioning component 302 receives the information from the one or more sensors. The signal conditioning component 302 converts the information from one or more analog signals to one or more digital signals. The one or more digital signals represent the motion of the one or more joints of the individual 102. The one or more digital signals are multiplexed to the signal processor 304. The signal processor 304 converts the one or more digital signals to the position information of the individual 102. The position information of the individual 102 derived from the signal processor 304 and the global positioning system 2 14 are passed to the inertial navigation system 212. The inertial navigation system 212 comprises an algorithm to weigh and combine the position information generated internally, and generated by the global positioning system 214 and the signal processor 304.

The steps or operations described herein are just exemplary. There may be many variations to these steps or operations without departing from the spirit of the invention. For instance, the steps may be performed in a differing order, or steps may be added, deleted, or modified.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention.

What is claimed is:

1. A method that uses a processing component to determine a change of location of an individual from a known starting location, the method comprising:
measuring articulation movements and twisting movements of one or more joints of an individual using corresponding strain sensors adjacent the one or more joints;
storing values corresponding to the measured articulation and twisting movements in a data storage medium;
determining, by the processing component, a change of displacement of the individual from the known starting location based on the stored values of the measured articulation movements relative to stored calibration factors of displacement and a change of directional location of the individual from the known starting location based on the stored values of the measured twisting movements relative to stored calibration factors of direction, where the calibration factors of displacement and direction define the relationship between the values of articulation and twisting movement and corresponding amounts of displacement and direction, respectively, of the individual;
integrating the strain sensors into a suit wearable by the individual;

determining the changed location of the individual relative to the known starting location based on the change of displacement and the change of directional location;

displaying the changed location of the individual on a display.

2. The method of claim 1, further comprising:

generating a path traversed by the individual based on a series of values corresponding to the measured articulation and twisting movements of the individual;

displaying the path of the individual on the display.

3. The method of claim 1, wherein the measured articulation movements comprises:

measuring a strain on a strain sensor induced on the strain sensor by movement of the joint adjacent to the strain sensor.

4. The method of claim 1, further comprising:

adding a series of the location changes of the individual to a known starting location of the individual to determine an updated location of the individual.

5. The method of claim 1, further comprising:

obtaining supplementary location information of the individual from one of an inertial navigation system and a global positioning satellite system; and weighing and combining the supplementary location information from the one or more supplementary navigation components and the changed location of the individual to generated an integrated location of the individual.

6. A method that uses a processing component to determine a path traversed by an individual, the method comprising:

measuring a series of articulation and twisting movements of one or more joints of an individual using strain sensors disposed near the one or more joints on the individual as the individual traverses the path;

integrating the strain sensors into a suit wearable by the individual;

storing articulation and twisting values corresponding to each measurement in the series of articulation and twisting measurements in a data storage medium;

converting the articulation and twisting values into corresponding changes of displacement and directional location, respectively, of the individual based on calibration factors of displacement and directional location obtained by storing articulation and twisting values while the individual is at known locations, where the calibration factors of displacement and direction define the relationship between the values of articulation and twisting movement and corresponding amounts of displacement and direction, respectively, of the individual;

determining locations of the individual along the path based on the changes of displacement and directional locations;

displaying the path traversed by the individual based on the locations of the individual along the path.

7. The method of claim 6, further comprising:

creating a map of an area using the path.

8. The method of claim 6, further comprising:

adding the location change of the individual to a known starting location of the individual to determine an updated location of the individual.

9. The method of claim 6, further comprising:

obtaining supplementary location information from one or more supplementary navigation components; and weighing and combining the supplementary location information from the one or more supplementary navigation components and the determined locations of the individual to generated an integrated location of the individual.

10. The method of claim 9, wherein the one or more supplementary navigation components comprise one or more components selected from the group consisting of a global positioning system ("GPS") and an inertial navigation system ("INS").

* * * * *